United States Patent
Rojo

(10) Patent No.: US 9,788,978 B2
(45) Date of Patent: Oct. 17, 2017

(54) IMPLANTABLE SYSTEMS AND STENTS CONTAINING CELLS FOR THERAPEUTIC USES

(76) Inventor: Nicholas A. Rojo, Jupiter, FL (US)

(*) Notice: Subject to any disclaimer, the term of this patent is extended or adjusted under 35 U.S.C. 154(b) by 1844 days.

(21) Appl. No.: 11/256,362

(22) Filed: Oct. 21, 2005

(65) Prior Publication Data

US 2006/0136049 A1      Jun. 22, 2006

Related U.S. Application Data

(60) Provisional application No. 60/637,054, filed on Dec. 20, 2004.

(51) Int. Cl.
*A61M 5/165* (2006.01)
*A61F 2/82* (2013.01)
*A61F 2/02* (2006.01)

(52) U.S. Cl.
CPC ............ *A61F 2/82* (2013.01); *A61F 2/022* (2013.01); *A61F 2250/0067* (2013.01); *A61M 2005/1652* (2013.01)

(58) Field of Classification Search
CPC ...... A61M 2005/1652; A61M 2202/04; A61M 2205/04
USPC ............... 623/1.41–1.43, 288.01, 288.04; 604/288.01, 288.04, 891.1, 892.1, 96.01, 604/103.01, 103.05
See application file for complete search history.

(56) References Cited

U.S. PATENT DOCUMENTS

| | | | |
|---|---|---|---|
| 3,313,289 A | | 4/1967 | Kapral |
| 3,794,026 A | * | 2/1974 | Jacobs ................. 128/200.13 |
| 4,084,588 A | * | 4/1978 | Koenig ................. 604/205 |
| 4,323,457 A | * | 4/1982 | Sun et al. ............ 210/645 |
| 4,437,856 A | * | 3/1984 | Valli ..................... 604/29 |
| 4,636,195 A | * | 1/1987 | Wolinsky ............. 604/509 |
| 5,030,216 A | * | 7/1991 | Theeuwes et al. .... 604/892.1 |
| 5,262,055 A | * | 11/1993 | Bae et al. ............. 210/645 |
| 5,571,189 A | * | 11/1996 | Kuslich ................ 623/17.12 |
| 5,702,444 A | * | 12/1997 | Struthers et al. ..... 623/23.64 |
| 5,716,404 A | * | 2/1998 | Vacanti et al. ....... 623/8 |
| 5,733,336 A | * | 3/1998 | Neuenfeldt et al. .. 435/325 |

(Continued)

FOREIGN PATENT DOCUMENTS

| | | |
|---|---|---|
| EP | 0757904 A1 | 2/1997 |
| WO | WO-99/55360 A1 | 11/1999 |

OTHER PUBLICATIONS

European Office Action mailed Mar. 1, 2010 in European Patent Application No. 05854702.7.

*Primary Examiner* — Paul Prebilic
(74) *Attorney, Agent, or Firm* — Venable LLP; Keith G. Haddaway; Annette K. Kwok

(57) ABSTRACT

An implantable system includes cells that produce and release a therapeutic agent, or agents, to a host in need. The system can include cells capable of eluting therapeutic agents in response to changing physiological conditions within a host. The system may comprise naked cells, encapsulated cells, or a mixture of non-encapsulating and encapsulated cells. The system may also comprise cells, and/or cell groups, of different origins. The implantable device may be placed intra-vascular, within bone marrow, within soft tissue, in the peritoneal cavity, or intra-hepatic, etc. The system can be comprised of a stent, or like devices. Such stents and like devices may optionally include port(s), catheter(s), and containment envelope systems for holding the above cells.

15 Claims, 6 Drawing Sheets

(56) References Cited

U.S. PATENT DOCUMENTS

| | | | |
|---|---|---|---|
| 5,787,900 A * | 8/1998 | Butler et al. | 128/898 |
| 5,824,053 A | 10/1998 | Khosravi et al. | |
| 5,843,069 A * | 12/1998 | Butler et al. | 604/891.1 |
| 5,843,172 A | 12/1998 | Yan | |
| 5,855,613 A * | 1/1999 | Antanavich et al. | 623/23.72 |
| 5,957,972 A | 9/1999 | Williams et al. | |
| 6,010,573 A | 1/2000 | Bowlin | |
| 6,117,166 A | 9/2000 | Winston et al. | |
| 6,206,914 B1 | 3/2001 | Soykan et al. | |
| 6,206,930 B1 * | 3/2001 | Burg et al. | 623/23.64 |
| 6,228,845 B1 | 5/2001 | Donovan et al. | |
| 6,955,661 B1 * | 10/2005 | Herweck et al. | 604/264 |
| 2002/0042597 A1 | 4/2002 | Hartlaub | |
| 2004/0148015 A1 | 7/2004 | Lye et al. | |
| 2005/0165354 A1 * | 7/2005 | Schwartz et al. | 604/152 |
| 2009/0069883 A1 * | 3/2009 | Ding et al. | 623/1.42 |
| 2013/0304031 A1 * | 11/2013 | Varner et al. | 604/521 |

* cited by examiner

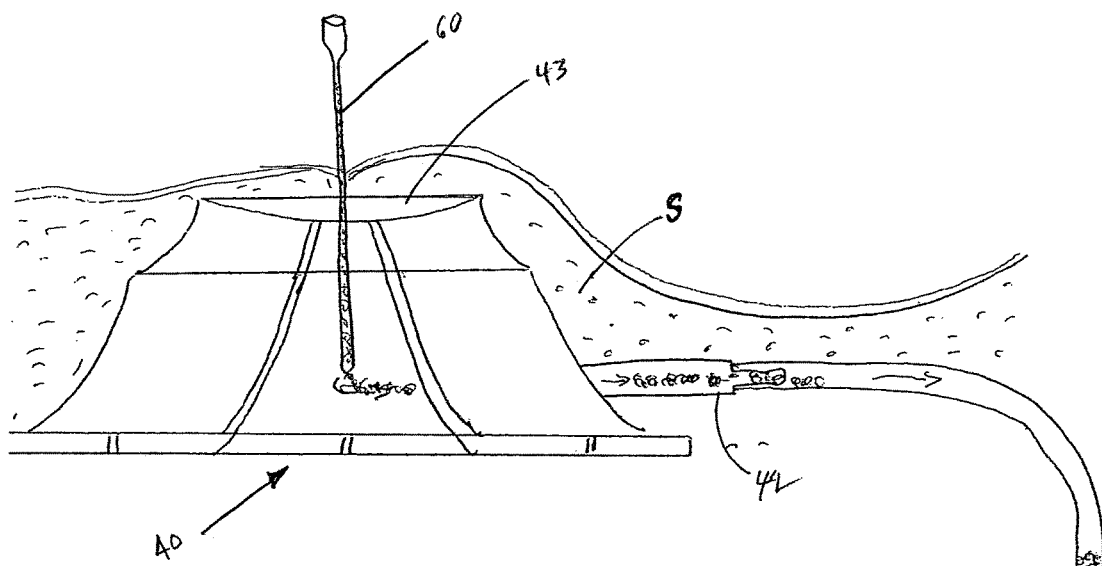
FIG 9
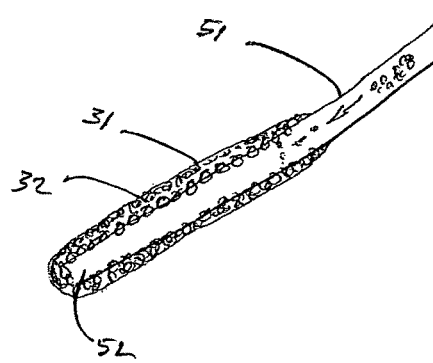

IMPLANTABLE SYSTEMS AND STENTS CONTAINING CELLS FOR THERAPEUTIC USES

RELATED APPLICATIONS

This application claims priority from the filing date of U.S. Provisional Application No. 60/637,054, filed Dec. 20, 2004.

FIELD OF THE INVENTION

The present invention relates to implantable systems that include various devices. Examples of such devices include stents, stent grafts, and vascular grafts. The devices contain cells capable of delivering therapeutic agents to a host in need. Such cells are optionally capable of producing and releasing a therapeutic agent in response to changing physiological cues within a host. Such stents and devices may optionally contain port, catheter, and containment envelope systems.

BACKGROUND OF THE INVENTION

Currently there are approximately forty models of stents available. Existing and proposed designs of stents address methods, drug elutions, and device innovations intended to combat common undesirable effects associated with stent graphs. Such effects include: thrombosis, vessel wall injury, intimal proliferation, and restenosis. The stent-related art almost exclusively focuses on a wide variety of ways to address the complications listed above that are common to stent procedures. A few researchers have even been designed stents that are seeded with endothelial cells prior to stent inplantation in the hopes that such endothelial cells will dampen the intimal proliferation observed in many stent procedures. The art, however, is void of teachings that address the seeding of stents with cells that could systematically deliver therapeutic agents to a host.

DESCRIPTION OF THE PRIOR ART

The art teaches various stent design methods which address thrombosis, vessel wall injury, intimal proliferation, and restenosis, including: Lau et al., "A stent is not just a stent: Stent construction and design do matter in its clinical performance.", Singapore Med J. 2004 July; 45(7):305-11; Morton et al., "The influence of physical stent parameters upon restenosis", Pathol Biol(Paris). 2004 May; 52(4):196-205; Lau K W et al., "Clinical impact of stent construction and design in percutaneous coronary intervention". Am Heart J. 2004 May; 147(5):764-73; Schiele F., "Predictive factors of restenosis: what changes with "active" stents?", Pathol Biol(Paris). 2004 May; 52(4):206-11.; Lau K W, et al., "Clinical impact of stent construction and design in percutaneous coronary intervention.", Am Heart J. 2004 May; 147(5):764-73; Silva M B, et al., "Technical note on renal angioplasty and stenting: new developments that facilitate its performance.", Vascular. 2004 January; 12(1):42-50.; Ong A T, et al., "Classification and current treatment options of in-stent restenosis. Present status and future prospectives.", Herz. 2004 March; 29(2):187-94; Kavanaugh C A, et al., "Local drug delivery in restenosis injury: thermoresponsive co-polymers as potential drug delivery systems.", Pharmacol Ther. 2004 April; 102(1):1-15.; Chong P H, Cheng J W., "Early experiences and clinical implications of restinosis and drug-eluding stents: Part 2.", Ann Pharmacother. 2004 May; 38(5):845-52; Froeschel M, et al., "Current understanding of in-stent restenosis and the potential benefit of drug eluting stents.", Curr Drug Targets Cardiovasc Haematol Disord. 2004 March; 4(1):103-17; Kereiakes D J, et al., "Thrombosis and drug-eluting stents: a critical appraisal.", Rev Cardiovasc Med. 2004 Winter; 5(1):9-15; Vishnevetsky D., et al., "Sirolimus-eluting coronary stent.", Am J Health Syst Pharm. 2004; 10(4):357-67:Sarembock I J, et al., "Stent restenosis and the use of drug-eluting stents in patients with diabetes mellitus.", Curr Diab Reo. 2004 February; 4(1):13-9; Bhatia V, et al., "Drug-eluting stents: new era and new concerns.", Postgrad Med J. 2004 January; 80(939):13-8; Woods T C Marks A R, "Drug-eluting stents.", Annu Rev Med. 2004; 55:169-78; Kereiakes D J, "Coronary small-vessel stenting in the era of drug elution.", Rev Cardiovasc Med. 2004; 5 Suppl 2:S34-45; Kester M, et al., "New strategies to prevent restenosis.", Am J Cardiovasc Drugs 2001; 1(2):77-83, McKeage K, et al., "The sirolimus-eluting stent: a review of its use in the treatment of coronary artery disease.", Am J Cardiovasc Drugs. 2003; 3(3):211-30; Laroia S T, Laroia A T, "Drug-eluting stents. A review of the current literature.", Cardiol Rev. 2004 January-February; 12(1):37-43; Smith E J, Rothman M T, "Antiproliferative coatings for the treatment of coronary heart disease: what are the targets and which are the tools?", Interv Cardiol. 2003 December; 16(6):475-83.

Other advances and attempts to build better stents and stent-like devices use brachytherapy and radiotherapy to combat in-stent restinosis. Additionally, drug-eluting stents [DES] (containing Rapamycin, paclitaxel, and the like), as exemplified by the Cyper stent and Taxus stent, were designed to release agents capable of quelling restenosis. Such techniques have been very effective—DES have lowered the rate of restinosis down to 10% or less in common practice. See: Lim M C, "Drug-eluting stents: the panacea for restenosis?", Singapore Med J. 2004 July; 45(7):300-2; Beyar R., "Novel approaches to reduce restenosis.", Ann N Y Acad Sci. 2004 May; 1015:367-78; Gowda R M, et al., "Efficacy and safety of endovascular intracoronary brachytherapy.", Int J. Cardiol. 2003 December; 15(12):732-4; Sheppard R, et al., "Intracoronary brachytherapy for the prevention of restinosis after percutaneous coronary revascularization.", Am Heart J. 2003 November; 146(5):775-86.

Another developmental path taken in the stent and stent-like device art is the application of agents pre- and post-stent treatment. With specific regard to thrombosis, the art teaches that anti-platelet agents are useful to dampen the risk of thrombosis—both pre- and post-stenting. See: Claeys M J., "Antiplatelet therapy for elective coronary stenting: a moving target.", Semin Vasc Med. 2003 November; 3(4):415-8; Medina R P, Foto D., "The use of bivalirudin to prevent subacute thrombosis during drug-eluting stent implantation.", J Invasive Cardiol. 2004 May; 16(5):236-9.

Yet another stent and stent-like device developmental effort recognized in the art relates to methods of preparing a lesion area to be stented prior to the stent insertion procedure. See: Moses J W, et al., "Lesion preparation prior to stenting.", Rev Cardiovasc Med. 2004; 5 Suppl 2:S16-21.

Another focus of the relevant art relates to methods regarding the placement of stents within a host. See: Faulknier B A, et al., "Clinical outcomes following IVUS-guided stent deployment in a community hospital." J. Invasive Cardiol. 2004 June; 16(6):311-5; Orford J L, et al., "Routine intravascular ultrasound guidance of percutaneous coronary intervention; a critical reappraisal.", J. Am Coll Cardiol. 2004 April 21; 43(8):1335-42.

The techniques for stent design in non-coronary stent placement methods generally parallel the concerns addressed by the art in coronary stent placement-namely thrombosis, vessel wall injury, intimal proliferation, and restenosis. Additional concerns in noncoronary stent placement focus on: 1) added structural tensions placed upon the stent in noncoronary locales, and 2) migration of the stent. See: Machan L., "Drug eluting stents in the infrainguinal circulation." Tech Vasc Interv Radiol. 2004 March; 7(1):28-32; Saxon R R, et al., "Endograph use in the femoral and popliteal arteries.", Tech Vasc Interv Radiol. 2004 March; 7(1):6-15; Morrissey N J., "Endovascular treatment of peripheral arterial aneurysms.", M t Sinai J. Med. 2004 January; 71(1):1-3; Costanza M J, et al., "Hemodynamic outcome of endovascular therapy for TransAtlantic InterSociety Consensus type B femoropopliteal arterial occlusive lesions.", J Vasc Surg. 2004 February; 39(2); 343-50; "Eliminating restenosis.", Mt Sinai J. Med. 2003 November; 70(6):417-9; Gravereaux E C, Marin M L., "Endovascular repair of diffuse atherosclerotic occlusive disease using stented graphs.", Mt Sinai J. Med. 2003 November; 70(6): 410-7; Chuter T A., "The choice of stent-graph for endovascular repair of abdominal aortic aneurysm.", J Cardiovasc Surg (Torino). 2003 August; 44(4):519-25.

U.S. Pat. No. 6,206,914 to Soykan teaches a technique to control the release of cellular components into the vascular tissue surrounding a stent. Such control may be mediated by an exogenous stimulus, examples of which include electrical signals.

U.S. Pat. No. 6,228,845 to Donovan teaches stents designed to deliver nucleic acids or virus to the wall of a lumen.

U.S. Pat. No. 5,843,069 to Butler and U.S. Pat. No. 5,787,900 to Butler teaches implantable devices that require surgical intervention, and all associated costs and risks encountered with general anesthesia, operating and recovery rooms. The devices described are not meant for intravascular deployment. The outer housing of the '069 devices comprise a polymer and the patent does not teach any material or techniques to protect the implanted therapeutic cells from the host's immune system. Finally, the devices taught have extracorporeal components, and thereby have an increased possibility for triggering infection in a host.

U.S. Pat. No. 6,010,573 to Bowlin teaches intravascular stents designed to minimize stent failure rates by the use of endothelial cells and/or engineered endothelial cells.

U.S. Pat. No. 6,117,166 to Winston teaches the use of stents for facilitating grafting of healthy blood vessel tissue.

U.S. Pat. No. 5,957,972 to Williams teaches the use of genetically modified endothelial cells, in conjunction with a stent, to inhibit the unwanted smooth muscle cell proliferation associated with many stent procedures.

Other researchers have discussed the use of cells, cellular material, or genetic material in conjunction with stents as a method to quell thrombosis, intimal proliferation, and restenosis. See: Schwartz R S, et al., "Biomimicry, vascular restenosis and coronary stents.", Semin Interv Cardiol. 1998 September-December; 3(3-4):151-6; Panetta C J, et al., "A tissue-engineered stent for cell-based vascular gene transfer.", Hum Gene Ther. 2002 February 10; 13(3):433-41; Dichek D A, et al., "Seeding of intravascular stents with genetically engineered endothelial cells.", Circulation 1989 November; 80(5):1347-53; Flugelman M Y, et al., "Genetically engineered endothelial cells remain adherent and viable after stent deployment and exposure to flow in vitro.", Circ res. 1992 February; 70(2):348-54; Shayani V, et al., "Optimization of recombinant t-PA secretion from seeded vascular grafts.", J Surg Res. 1994 October; 57(4):495-504; Shirota T, et al, "Fabrication of endothelial progenitor cell (EPC)-seeded intravascular stent devices and in vitro endothelialization on hybrid vascular tissue.", Biomaterials. 2003, "Immortalized human microvascular endothelial cells.", Am Heart J. 1995 May; 129(5):860-6; Consigny P M., "Endothelial cell seeding on prosthetic surfaces.", J Long Term Eff Med Implants. 2000; 10(1-2):79-95.

The art does not include teachings to the design or use of stent and stent-like devices that contain cells, or cellular components, that are able to deliver a therapeutic element to a host in response to the physiology of the host. The few teachings that include stents with contained cells, or cellular components, are limited to methods and devices designed to combat the art-recognized problems associated with stent and stent-like devices. Such problems include thrombosis, vessel wall injury, intimal proliferation, and restenosis. The art also does not disclose teachings to the design and use of stent and stent-like devices capable of delivering therapeutic elements, compounds, etc. to a host in response to changing physiological states within the host.

The complete disclosures of the patents, patent applications and publications listed herein are incorporated by reference, as if each were individually incorporated by reference.

SUMMARY OF THE INVENTION

The above art is devoid of teachings that address the seeding of stents with cells that could systematically deliver therapeutic agents to a host. The instant invention meets these and other needs.

Accordingly, it is a primary objective of the instant invention to provide an implantable system that includes cells that produce and release a therapeutic agent, or agents, to a host in need. The system can include cells capable of eluting therapeutic agents in response to changing physiological conditions within a host. The system may comprise naked (non-encapsulated) cells, encapsulated cells, or a mixture of non-capsulated and encapsulated cells. The system may also comprise cells, and/or cells groups, of different origins. The system may be placed intravascularly, within bone marrow, within soft tissue, in the peritoneal cavity, intra-hepatically, etc. Such stents and devices may optionally contain a port, catheter(s), and containment envelope systems. Finally, the system can be comprised of a stent, and like devices.

It is a further objective of the instant invention to provide intraluminal stents having a lumen-wall contacting surface and a lumen-exposed surface wherein the stent is suitable to deliver therapeutic agents to host in response to changing physiological states of a host. The invention also relates to methods for making stents and to methods for delivering therapeutic agents to a host from such stents.

It is yet another objective of the instant invention to provide ports, catheters and containment envelopes to be used with the devices and stents described in the invention.

A useful port is one that comprises an access device that allows transdermal infusion of cells, cell substrates, therapeutic agents, etc. into a reservoir, or containment envelope, within the devices or stents of the present invention. Such ports can be dual or single. If dual, the port system allows for the addition, or deletion of cells, cell substrates, or therapeutic agents. The port can be placed within the subcutaneous tissues and therefore eliminate the need for transcorporeal component(s). The port can be made of plastic, titanium, or other materials known in the art and may optionally have a transdermal puncture piercing into the port by way of a traversing diaphragm.

A useful catheter system to be used with the devices or stents of the present invention, can include multi side-holed, open ended catheter(s) capable of communicating with an outer envelope or other containment device(s). Intravascular placement can be performed via a femoral, jugular, cephalic, basilic, subclavian venous, etc. approach. The tip of the catheter(s) can be placed, among other locations, in major venous structure(s) such as the inferior vena cava or superior vena cava.

A useful containment envelope system to be used with the devices or stents of the present invention can be composed of a porous polymer, alginate, or other materials known to one of skill in the art. The reservoir wall typically envelopes the distal end of the catheter, and a small space is created between the catheter and the outer reservoir wall. Here the cells, cellular components, or therapeutic agents rest. The containment envelope optionally creates an immuno-barrier thereby shielding the cells from the host's immune system, while allowing for exchange of nutrients to the cells from surrounding body fluids.

It is a still further objective of the instant invention to provide several embodiments of use. In an embodiment, the present invention provides an implantable system comprising an intraluminal stent, which includes a lumen-wall contacting surface, a lumen-exposed surface, a first matrix composition covering at least a portion of the stent and cells associated with the first matrix composition covering, wherein the cells produce at least one therapeutic agent in response to changing physiological signals within a host.

In another preferred embodiment such as an implantable system is optionally equipped with a port and catheter system capable of adding or deleting cells, cellular components, or therapeutic agents to and from the device or stent.

In another preferred embodiment such an implantable system is optionally equipped with a port and catheter system capable of adding or deleting cells, cellular components, or therapeutic agents to and from the device or stent, wherein the device or stent has a containment envelope accessible to such a port and catheter.

Another objective of the instant invention provides a method of systematic delivery of a therapeutic agent.

The method involves implanting an implantable system described above. Once implanted into a host, the therapeutic agent(s) is released from the device in response to a physiological property (e.g., a blood glucose level, etc.)

Also, an objective of the instant invention is a method of making an implantable system for distal delivery of a therapeutic agent is included within the scope of the present invention. This method includes: providing a delivery device comprising a carrier and encapsulated or non-encapsulated cells that produce at least one therapeutic agent; and contacting the cell(s) with the host in such a manner that the cells can respond to the changing physiology of the host and stimulate the release of therapeutic agent(s) to said host. Preferably, the step of providing a delivery device includes: providing a carrier; isolating cells from an animal or human donor; and contacting the carrier of the cells.

In an embodiment the device(s) can be implanted with minimum invasiveness and can be entirely retrieved percutaneously.

In an embodiment the device(s) is intended and designed for intravascular deployment (venous/arterial).

In an embodiment the inner housing of the device(s) is composed of titanium.

In an embodiment the outer housing of the device(s) are composed of titanium for greater protection of the inner housing and the introduced cells (or other therapeutic substances). Given that titanium is radiopaque, the location and configuration of the implanted device(s) can be monitored, located, etc. using inexpensive conventional imaging.

In an embodiment, the device is deployed in bone, soft tissue, intraperitoneal, and hepatic tissues. In such deployments, the containment vehicle consists of a reservoir comprising a porous polymer, or polymers, capable of allowing nutrient and waste exchanges with surrounding medium and tissues. The containment vehicle contains cells, cells substrates, pharmacologically active substances, or radioactive therapeutic materials. The containment vehicle can be housed by a titanium stent or cage for additional physical protections. Such stent and cages can also serve to protect the surrounding medium from overgrowth of the containment device.

In an embodiment, the device has a containment vehicle that can be flushed, emptied, or replenished by way of an attached catheter. The catheter is accessed by way of a port that is implanted in the superficial subcutaneous tissues. The port can be accessed by a needle, or similar technique, as recognized in the art. The implantation of the entire module can be performed with a less invasive approach, as compared with existing methods found in the art. Such a port and catheter approach can be performed with a local anesthetic administration to a host, and therefore, obviate the need for more conventional, and invasive, surgical approaches.

In an embodiment, the device has no extracorporeal components. Generally, extracorporeal components associated with any implantable device increase the chance for infection and sepsis. If any component of an implanted device gets infected then the entire device has to be removed.

In an embodiment, release if the therapeutic agent(s) from the device is stimulated by a variety of physiological inputs and, or, changes within a host.

In an embodiment, the physiological input from the host to the device is mediated via levels of chemicals, agents, signaling molecules, etc. within the blood, and, or other fluid of the host.

Thus, an object of the present invention is to provide a method and system for treating, and in some embodiments, preventing, various disorders, for example, by producing and systematically delivering a therapeutic agent or agents, such as insulin.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 9 illustrates a non-coring transdermal needle placed in a port, replenishing a containment envelope with a therapeutic substance, or cells according to an embodiment of the invention.

DETAILED DESCRIPTION OF THE INVENTION

Figure 1:
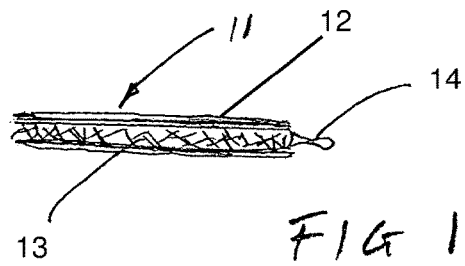
FIG. 1 illustrates a collapsed stent preloaded with encapsulated cells for intra-arterial deployment and having a loop for retrievably, according to an embodiment of the invention.

The present invention provides implantable systems for the treatment (including prevention) of a variety of disorders, such as, diabetes, leukemias, immune disorders, metabolic disorders, malignancies, hormone disorders, arthritis, hypertension, etc. The implantable systems of the present invention include a delivery device 10 comprising a carrier (e.g., stents, vascular grafts, stent graphs) and cells 20 (e.g., encapsulated cells, non-encapsulated cells, engineered cells), which can optionally be enclosed within containment vehicles 30. Such cells 20 are capable of responding to changing conditions within a host and producing one or more therapeutic agents in response to such conditions. The produced agents may have a therapeutic, preventative, or disease-modifying effect on the host.

The therapeutic agents are released from the cells of the delivery device upon the receipt of a stimulus, or contact of an endogenous signal or chemical, from the host (changes in blood glucose concentrations, changes in blood levels of a hormone, metabolic signaling agent, chemical signaling molecules, etc).

Cells 20 suitable for use in the present invention include a wide variety of cells that produce therapeutic agents. Such cells are able to secrete these agents upon the receipt of an endogenous signal received by the host. Suitable cells for use in the present invention typically include islets cells, endocrine cells, immune system cells, bone marrow cells, thyroid cells, mast cells, dermal cells, nervous system cells, skin cells, and other cells that would be recognized by one of skill in the art, whether they are autologous or allogeneic, genetically engineered or nonengineered. Mixtures of such cells can also be used.

There are a variety of disorders that can be treated using the systems and devices of this invention. Examples of these disorders include, but are not limited to: metabolic disorders, diabetes, arthritis, hypertension, nervous system disorders, immune system disorders, chronic pain, endocrine disorders, inflammations, amyloidosis, acute leukemias, chronic leukemias, myelodysplastic syndromes, stem cell disorders, myeloproliferative disorders, lymphoproliferative disorders, phygocyte disorders, inherited metabolic disorders, histiocytic disorders, erythrocyte abnormalities, immune disorders, platelet abnormalities, plasma cell disorders, malignancies (breast carcinoma, Ewing Sarcoma, neuroblastoma, renal cell carcinoma, etc.), hypothyroidism, hypopituitarism, hypogonadism, graph failure, graph versus host disease (GVD), veno-occlusive disease, side effects form pre-transplant chemotherapy (mouth sores, hair loss, pancytopenia, neutropenia, infections, bleeding, infertility, catatacts, renal as well as lung and heart complications, and recurrent disease), and other disorders and diseases that would be recognized by one of skill in the art.

Therapeutic agents can be secreted by the cells contained in the devices described herein. Such cells are referred to herein as "drug-eluting" cells. Such cells may be useful for a wide-variety of functions such as: delivering pharmacoactive substances for treatment of local, regional, or systematic disease; promoting new cell production; adding to a depleted marrow cell line; activating cell function; buffering or blocking a specific cell dysfunction; altering, treating or influencing oncogenesis; contributing to enhancement of a local cell population; gene therapy; tumor specific vaccinations; delivering of a specific radionuclide labeled therapeutic agent (resulting in more efficacious local radiation dose with fewer or no systemic side effects; delivery of therapeutic agent to the epicenter of a tumor, and other functions as would be recognized by one of skill in the art.

The drug-eluting cells can be incorporated into the carrier 11 or incorporated into the coating of the device or stent. They can also be included within a containment apparatus 30. The apparatus can be coated on the carrier or incorporated into the carrier of the device or stent. The cells can be induced to release one or more therapeutic agents in response to a signal from the host. Such signals can embody a wide variety of physiologic events, chemicals, signaling agents, cellular messengers, inputs, etc. as would be appreciated by one of skill in the relevant art.

The modules and devices 10, shown in FIG. 1-4, herein can be percutaneously introduced using known and common radiological techniques and imaging devices (fluoroscopy, CAT scans, MRI, etc). The radiopaque nature of the devices described herein allows for follow-up imaging. The composition of the devices (e.g., titanium) allows for a biocompatible, nonferromagnetic structure. Implantation techniques may only require a simple local anesthetic and can be performed in minutes. The containment function of the module avoids rapid decrease in function and or cell population. Thus, the structural and unit integrity of the transplanted material is maintained. The required therapeutic response can be enhanced or altered by removal, replacement or addition of other modules as needed.

As used herein, a "delivery device" 10 includes: cells that produce one or more therapeutic agents, a carrier (e.g., stent, stent graph, vascular graft, bone graft, hepatic graph, etc.), optional containment vehicles, and other, optional, therapeutic and, or, non-therapeutic materials.

Figure 2:
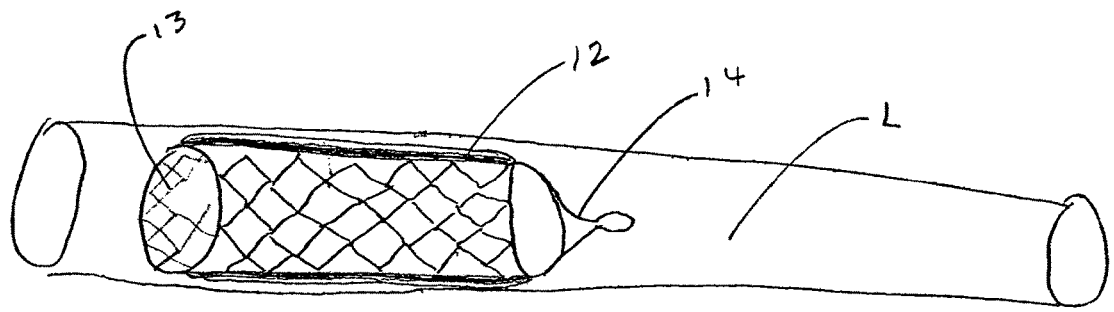
FIG. 2 illustrates the stent of FIG. 1 in expanded form, deployment in a blood vessel.

The term "stent" 11 refers to any device capable of being placed into contact with a wall of lumen L. FIG. 1 illustrates a collapsed stent according to an embodiment of the invention. The inner layer 13 of the stent can be made of a titanium mesh, for example. The outer layer 12 of the stent can also be a titanium mesh, or it can be made of pervious "Gore-tex" or other suitable material. Such a stent can be used for intra-arterial deployment in an embodiment of the invention. The diameter of the collapsed stent can be approximately 2-5 mm. FIG. 2 illustrates the stent of FIG. 1, in expanded form, as deployed in an artery lumen L. In an embodiment of the invention, the stent is pre-loaded with pancreatic islet cells.

Figure 3:
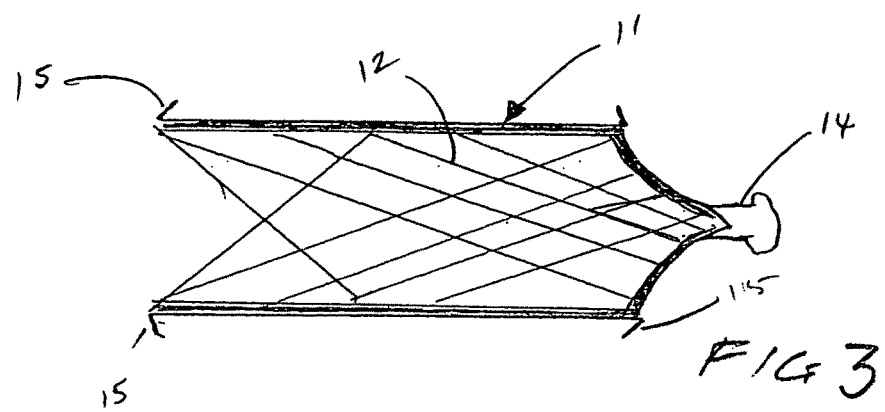
FIG. 3 illustrates an expanded intravenous stent with a loop for retrievably and fixating barbs, with an outer wall of titanium or "Gore-tex".
Figure 4:
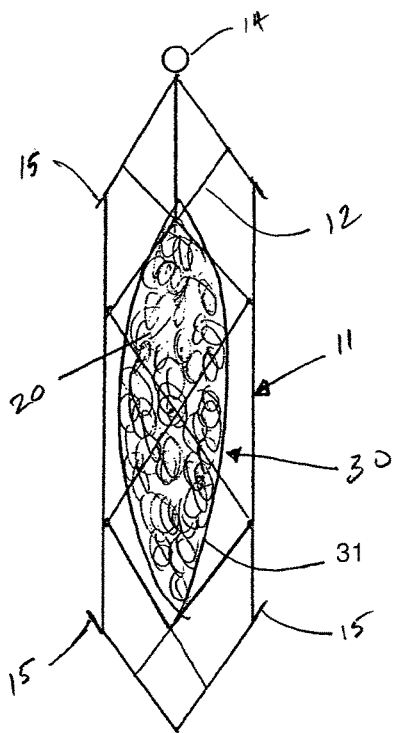
FIG. 4 illustrates an expanded retrievable bone, hepatic, and peritoneal cell transplantation module with fixation barbs and containing a sac of cells, where the sac is made of an alginate or a porous polymer, according to an embodiment of the invention.
Figure 5:
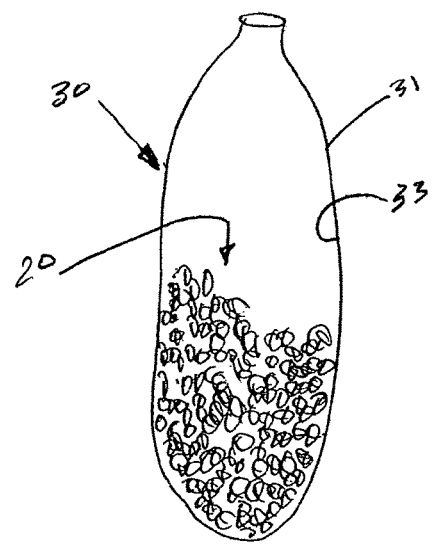
FIG. 5 illustrates an inner cell containment reservoir, composed of a porous polymer or alginate material, according to an embodiment of the invention.

Generally, when the device is shaped like a stent, it is designed in a tube-like fashion and has a lumen wall-contacting surface 12 and a lumen-exposed surface 13. The lumen-wall contacting surface is the outside surface of the tube while the lumen-exposed surface is the inner surface of the tube. After insertion by catheter, in a lumen L, the collapsed mesh tube, shown in FIG. 1, is expanded, as by a balloon, to remain in the lumen, as shown in FIG. 2. The stent may have a loop 14 for retrieving and/or fixing in place. Also, for positioning and retention, the stent may have barbs 15 that embed in the lumen walls. FIG. 3-4 illustrate an embodiment of the invention featuring pre-loaded encapsulated calls and fixation barbs 15 usable in hepatic and bone implantation. As before, both inner and outer lattices can be made of titanium.

The stent can generally include metallic or polymeric elements, or be combinations thereof. One of skill in the art can use of many varied materials to build a device, or devices, that can be used in the present invention.

FIG. 4 illustrates an expandable retrievable module for bone, hepatic, or peritoneal cell implantation. The module contains a sac 30 of cells. The sac 30 can be made of an alginate or a porous polymer material 31. Fixation barbs 15 are also shown and such barbs would be useful for bone or hepatic implantation.

As used herein the term "port" 40 refers to the device that allows transdermal infusion if cells, cell substrates, therapeutic agents, etc. into a reservoir or containment envelope within the devices or stents of the present invention. Such ports can be dual 41 or single 40. The dual port system 41 allows for the addition, or deletion of, cells, cell substrates, or therapeutic agents. The ports can be placed within the subcutaneous tissues S and therefore eliminate the need for trans-corporeal component(s). The ports can be made of plastic, titanium, or other materials known in the art and may optionally have a transdermal puncture piercing into the port by way of a traversing diaphragm 43.

As used herein the term "catheter" 50 refers to a device that is capable of communicating with the devices, port(s), stents, and containment device(s) as described herein. Intravascular placement can be performed via a femoral, jugular, cephlic, basilic, or subclavian venous approach. The catheter(s)tip 52 can be placed, among other locations, in major venous structure(s) such as the inferior vena cava or superior vena cava. The catheter 50 may be secured to the port 40 at the outlet 42.

As used herein the term "containment envelope" 32 refers to a structure that can be used as part of, or with, the devices, catheter(s) or stents of the present invention. The containment envelopes 32 can be composed of a porous polymer, alginate, or other materials known to one of skill in the art. Typically, such envelopes comprise a space that is created between the catheter's outer wall 51 and the containment envelope's inner wall 33. The space is where the cells, cellular components, or therapeutic agents rest. The containment envelope optionally creates an immuno-barrier capable of shielding contained cells from the host's immune system, while allowing for exchange of nutrients to the contained cells from surrounding body fluids. The containment envelope can also be referred to as a containment vehicle or reservoir.

In one embodiment of the invention, a stent may have cells that can be replenished. A sac 30 is located within the stent to be replenished by catheter. The reservoir can be made of a porous polymer or alginate material. The porous reservoir allows the transfer of nutrients from the surrounding medium to the cells, and permits the release of cells wastes through the reservoir wall.

Figure 6:
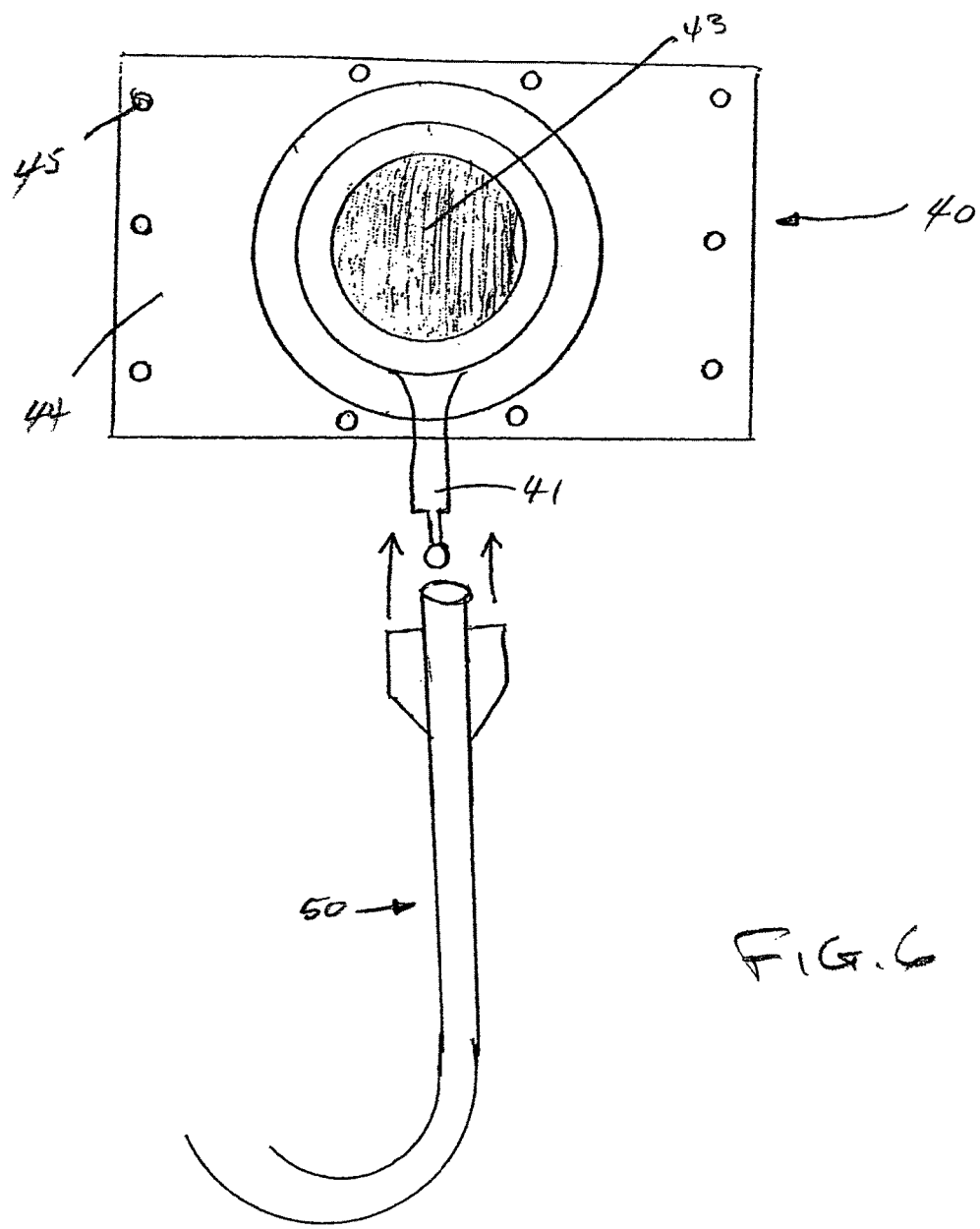
FIG. 6 illustrates an implantable port that provides transdermal access to an inner cell reservoir through a single lumen catheter, according to an embodiment of the invention.
Figure 7:
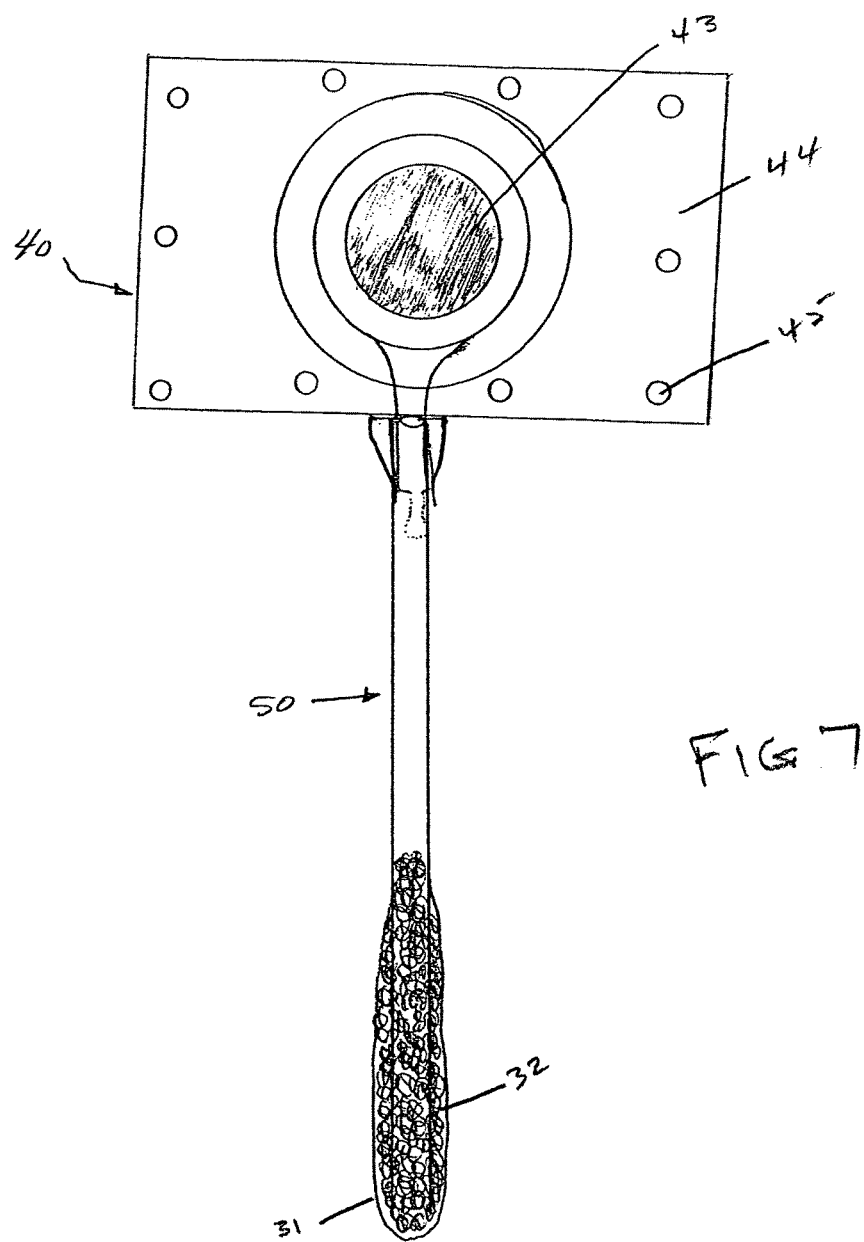
FIG. 7 illustrates a singular port that is implantable in subcutaneous tissue and that serves to access, replenish, and/or drain a cell containment envelope, according to an embodiment of the invention.

In the illustrated embodiment of FIG. 6-7, an approximate rectangular base 44 is shown surrounding the port, and features perforations 45 around the perimeter of the base to allow suturing to subcutaneous tissue S. The catheter 50 is shown attached to the port at one end. The opposite end of the catheter connects to the reservoir shown in FIG. 7-9. The reservoir may in turn reside in a stent.

Figure 8:
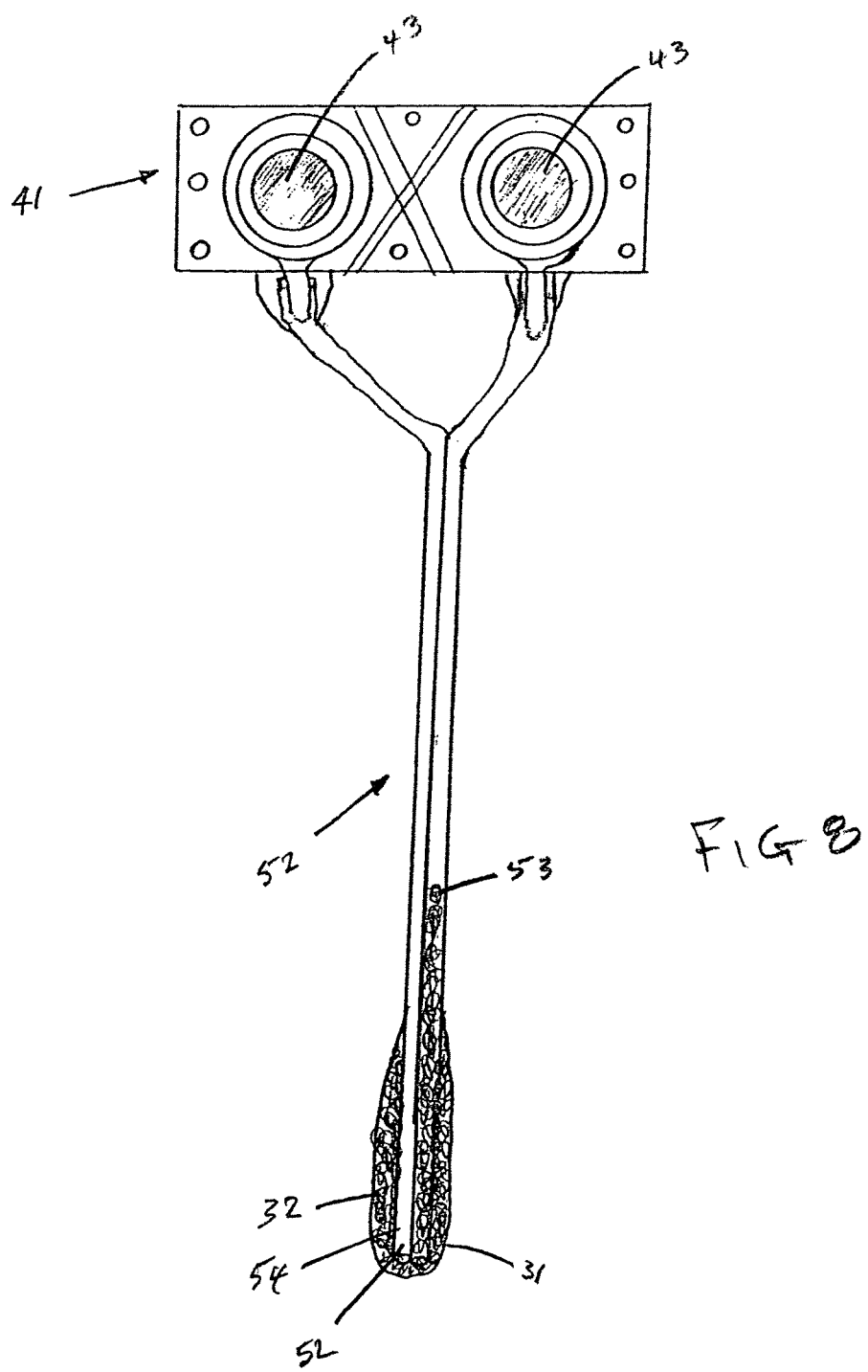
FIG. 8 illustrates a dual port that allows for flushing and/or simultaneous infusion of therapeutic cells into a containment envelope while removing old cells or expended therapeutic agent, according to an embodiment of the invention.

In an alternative embodiment of the invention, a dual port 41, shown in FIG. 8, can be used instead of a singular port. This configuration allows simultaneous access to the reservoir from two separate points. The dual port allows for flushing and/or simultaneous infusion of therapeutic cells into the reservoir while removing old cells or expended therapeutic agent. The dual port embodiment can be connected to a double lumen catheter 52. In this illustration, the catheter on the right is used for the provision of new cells into a reservoir. This process is facilitated by a presence of openings, or sideholes, 53 in the lower end of the catheter, such that cells can flow from the catheter on the right through the openings into the reservoir. The catheter on the left can be used to remove old cells or expended therapeutic agent. The removal process is likewise facilitated by the presence of openings 54 in the lower end of the catheter on the left. In the illustrated embodiment, the reservoir can be pre-loaded with cells prior to implantation.

FIG. 9 illustrates the use of a non-coring transdermal needle 60 in the port assembly 40. The needle can be used to replenish the reservoir or containment envelope at the distal end of the catheter. This assembly can be deployed, for example, with the catheter tip in the superior vena cava.

What is claimed is:

1. A medical device comprising:
   an elongated catheter comprising an intravascularly implantable tip end and a port end; and
   a porous sac radially disposed about and enclosing said tip end thereby forming a containment envelope between said sac and said tip end; said tip end having openings or side holes in communication with said containment envelope within said sac; said sac capable of eluting one or more therapeutic agents that elute through said sac in response to a stimulus when biologically active cells for containing one or more therapeutic agents are optionally disposed in said containment envelope.

2. A medical device of claim 1, wherein said catheter is composed of two lumens, one of said lumens for providing nutrient to said containment envelope and the other lumen for removing waste from said containment envelope.

3. A medical device of claim 1, wherein the port end of said catheter is connected to a port providing a transcutaneous passageway, said port having a base for attachment to the host, said port having an inlet covered with a diaphragm, said inlet connected to an outlet, said catheter connected to said outlet.

4. A medical device of claim 1, wherein the device is designed for intravascular deployment via venous or arterial approach.

5. A medical device of claim 1, wherein the device is designed for intravascular placement that is performed via a femoral, jugular, cephalic, basilic, or subclavian venous approach.

6. A medical device of claim 1, wherein the device is connected to a port for adding cell components to said device.

7. A medical device of claim 1, wherein the device is designed for intravascular placement and is connected to an implantable port that provides transdermal access to said intravascularly placed device.

8. A medical device of claim 1, wherein the device further comprises a stent.

9. A medical device of claim 1, wherein the cells comprise islets cells, endocrine cells, immune system cells, bone marrow cells, thyroid cells, mast cells, dermal cells, nervous system cells, or skin cells.

10. A medical device of claim 1, wherein the therapeutic agent is for: treating local, regional, or systematic disease; promoting new cell production; adding to a depleted marrow cell line; activating cell function; buffering or blocking a specific cell dysfunction; altering, treating or influencing oncogenesis; contributing to enhancement of a local cell population; gene therapy; or tumor specific vaccinations.

11. A medical device of claim 1, wherein the therapeutic agent is insulin.

12. A medical device of claim 1, wherein the sac comprises an alginate or a porous polymer.

13. A medical device of claim 1, wherein the stimulus is a change in blood glucose concentration, a change in blood level of a hormone, a metabolic signaling agent or a chemical signaling molecule.

14. A medical device of claim 8, wherein the stent has a diameter of approximately 2-5 mm when collapsed.

15. A medical device comprising:
    an implantable portion comprising:
        an elongated catheter comprising an intravascular tip end and a port end; and
        a porous sac radially disposed and encompassing the intravascular tip end thereby forming a containment envelope between the sac and the tip end, the tip end having openings or side holes in communication with the containment envelope within the sac, the sac capable of eluting one or more therapeutic agents through the sac in response to a stimulus when biologically active cells for containing one or more therapeutic agents are optionally disposed in the containment envelope, and the sac allowing transfer of nutrients from medium surrounding the sac to the cells; and
    a port connecting to the port end of the elongated catheter.

* * * * *